United States Patent [19]

Wiegers et al.

[11] Patent Number: 4,490,544

[45] Date of Patent: Dec. 25, 1984

[54] MACROCYCLIC CARBONATES, PROCESSES FOR PREPARING SAME, ORGANOLEPTIC USES THEREOF AND INTERMEDIATES USED IN SAID PROCESS

[75] Inventors: Wilhelmus J. Wiegers, Red Bank, N.J.; Augustinus G. Van Loveren, Rye, N.Y.; Marie R. Hanna, Hazlet, N.J.; Domenick Luccarelli, Jr., Neptune, N.J.; David R. Bowen, Red Bank, N.J.; Manfred H. Vock, Locust, N.J.

[73] Assignee: International Flavors & Fragrances Inc., New York, N.Y.

[21] Appl. No.: 511,909

[22] Filed: Jul. 8, 1983

[51] Int. Cl.³ .............................................. C07D 321/00
[52] U.S. Cl. .................................. 549/228; 252/522 R
[58] Field of Search ........................................ 549/228

[56] References Cited

U.S. PATENT DOCUMENTS

| | | | |
|---|---|---|---|
| 2,020,298 | 11/1935 | Carothers et al. | 549/228 |
| 4,218,379 | 8/1980 | Harris et al. | 549/228 |
| 4,331,603 | 5/1982 | Harris | 549/228 |

OTHER PUBLICATIONS

Jiro Tsuji et al., Journal of Organometallic Chemistry, vol. 218 (1981), pp. 69–80.
Steffen Arctander, Perfume and Flavor Chemicals, vol. I publ. by the Author, Montclair, N.J. (USA) (1969) Sections 105, 106, 107, 1445.

*Primary Examiner*—Norma S. Milestone
*Attorney, Agent, or Firm*—Arthur L. Liberman

[57] ABSTRACT

Described is a class of macrocyclic carbonates defined according to the structure:

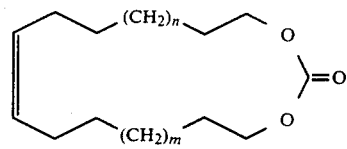

wherein n is an integer of from 1 up to 8 and m is an integer of from 1 up to 8 and where n and m may be the same or different and organoleptic uses thereof in augmenting or enhancing the aroma or taste of foodstuffs, chewing gums, toothpastes, medicinal products, chewing tobaccos, perfume compositions, colognes and perfumed articles (i.e. solid or liquid anionic, cationic, nonionic or zwitterionic detergents, fabric softener compositions, fabric softener articles, cosmetic powders and perfumed polymers).

1 Claim, 7 Drawing Figures

NMR SPECTRUM FOR EXAMPLE I.

GLC PROFILE FOR EXAMPLE II. FIRST DISTILLATION PRODUCT.

MACROCYCLIC CARBONATES, PROCESSES FOR PREPARING SAME, ORGANOLEPTIC USES THEREOF AND INTERMEDIATES USED IN SAID PROCESS

BACKGROUND OF THE INVENTION

The present invention relates to macrocyclic carbonates defined according to the generic structure:

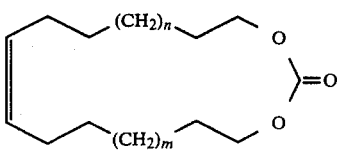

wherein n and m are the same or different and each represents an integer of from 1 up to 8 as well as organoleptic uses thereof to alter, modify, augment, enhance or impart flavors and/or aromas in (or to) consumable materials.

There has been considerable work performed relating to substances which can be used to impart (or alter, modify or enhance) flavors and fragrances to (or in) various consumable materials. These substances are used to diminish the use of natural materials some of which may be in short supply and to provide more uniform properties in the finished product. Sweet and musky aroma characteristics and sweet and musky flavor characteristics are particularly desirable for uses in flavors particularly pear, peach, tropical fruit (e.g. mango) and blackberry flavors. Musky aromas are desirable in several types of perfume compositions and for use in perfumed articles.

Macrocyclic lactones and macrocyclic ketones are well known in the field of perfumery and are also well known for uses in food flavors. Thus, U.S. Pat. No. 4,282,274 issued on Aug. 4, 1981 discloses organoleptic uses (flavors and fragrances) of 2- and 3-cyclotetradecen-1-ones.

Metathesis reactions to produce such musk-type materials are also known in the prior art. Thus, Tsuji and Hashiguchi, J. Organometallic Chemistry, 218 (1981) 69–80 discloses the following reaction to prepare 10-eicosen-20-olide:

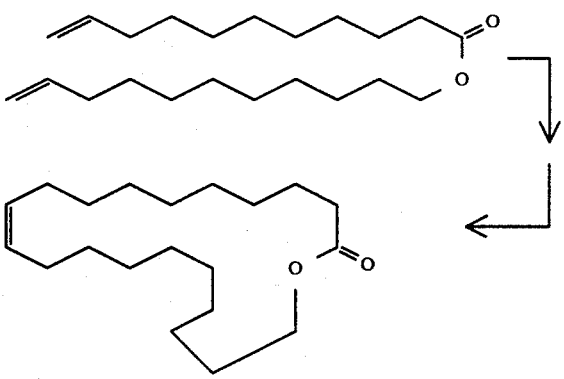

Ambrettolide is disclosed by Arctander "Perfume and Flavor Chemicals (Aroma Chemicals) Volume I" published in 1969 at monograph 105 to have extensive use as a modifier-blender in flavor compositions, particularly in alcoholic beverages. Arctander also discloses ambrettolide to be useful as a fixative in perfumes and flavors and to have by itself extremely tenacious floral-musky sweet odor. Ambrettolide has the structure:

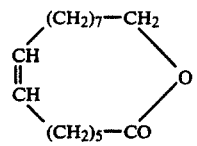

At sections 106 and 107, Arctander discloses $\Delta^5$-iso-ambrettolide having the structure:

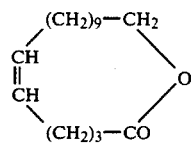

and $\Delta^6$-iso-ambrettolide having the structure:

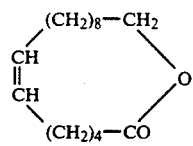

indicating limited use in perfumery for these materials.

The prior art contains a large number of teachings regarding the use of organic carbonates in augmenting or enhancing the aroma of perfumes. Thus, U.S. Pat. No. 4,033,993 discloses the use of organic carbonates defined according to the structure:

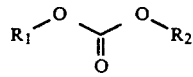

wherein $R_1$ is a moiety having from 8 to 12 carbon atoms selected from the group consisting of alkylcyclohexyl, alkenylcyclohexyl, alkynylcyclohexyl and cycloalkyl and $R_2$ is a moiety selected from the group consisting of alkyl having from 1 to 5 carbon atoms, alkenyl having from 2 to 5 carbon atoms and alkynyl having from 2 to 5 carbon atoms. U.S. Pat. No. 4,033,993 describes, for example, methyl-1-ethynycyclohexyl carbonate having a fruity, herbal complex odor and distinct fragrance of dill. In addition, U.S. Pat. No. 4,033,993 describes methyl cyclooctyl carbonate as having an herbal, natural and complex fragrance which is distinguished by a strong and long clinging flowery jasmine scent and further indicates its use in jasmine perfume compositions. U.S. Pat. No. 4,033,993 describes the preparation of the compounds defined according to the structure:

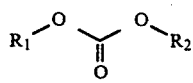

according to the reaction:

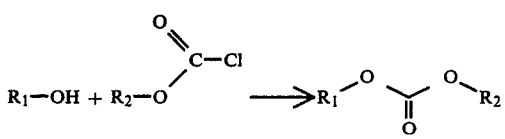

where $R_1$ and $R_2$ are defined as above.

In addition, U.S. Pat. No. 4,080,309 describes the perfume use of the carbonates defined according to the structure:

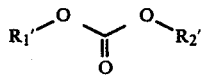

wherein $R_1'$ is a moiety having from 8 to 12 carbon atoms selected from the group consisting of alkylcylohexyl, alkenylcyclohexyl, alkynylcyclohexyl and cycloalkyl and $R_2'$ is a moiety selected from the group consisting of alkyl having from 1 to 5 carbon atoms, alkenyl having from 2 to 5 carbon atoms and alkynyl having from 2 to 5 carbon atoms. Described in U.S. Pat. No. 4,080,309 are also such compounds as methyl cyclooctyl carbonate and the use thereof in jasmine perfume formulations. As is the case in U.S. Pat. No. 4,033,993, the carbonates of U.S. Pat. No. 4,080,309 are indicated to be prepared according to the reaction:

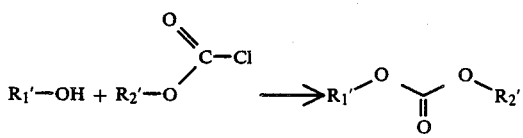

Geranyl ethyl carbonate is disclosed by Arctander "Perfume and Flavor Chemicals (Aroma Chemicals), Volume I" published in 1969 at monograph No. 1445 to have a "sweet and mellow, rosey and warm tenacious odor . . . sweeter than geraniol but not fruity like geranyl acetate, rather mellow in an almost musky way . . . ". Although geranyl ethyl carbonate is an adjacent methyl homologue of geranyl methyl carbonate of the instant invention, the geranyl methyl carbonate has properties in the perfumery art which are considered to be unexpected, unobvious and advantageous. Thus, the citrusy, floral, rosey, muguet, geranium aroma of geranyl methyl carbonate is advantageous and distinct from the "sweet and mellow rosey and warm tenacious odor" of geranyl ethyl carbonate.

Nothing in the prior art, however, discloses the macrocyclic carbonates of our invention or intermediates for preparing said macrocyclic carbonates or processes for preparing said macrocyclic carbonates or organoleptic uses thereof.

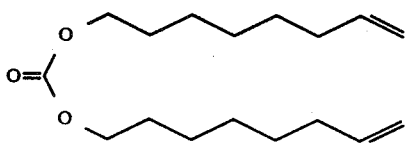

produced according to Example I (bulked distillation fractions 3-11) (conditions: Field Strength: 100 MHz; Solvent $CFCl_3$).

Figure 2:
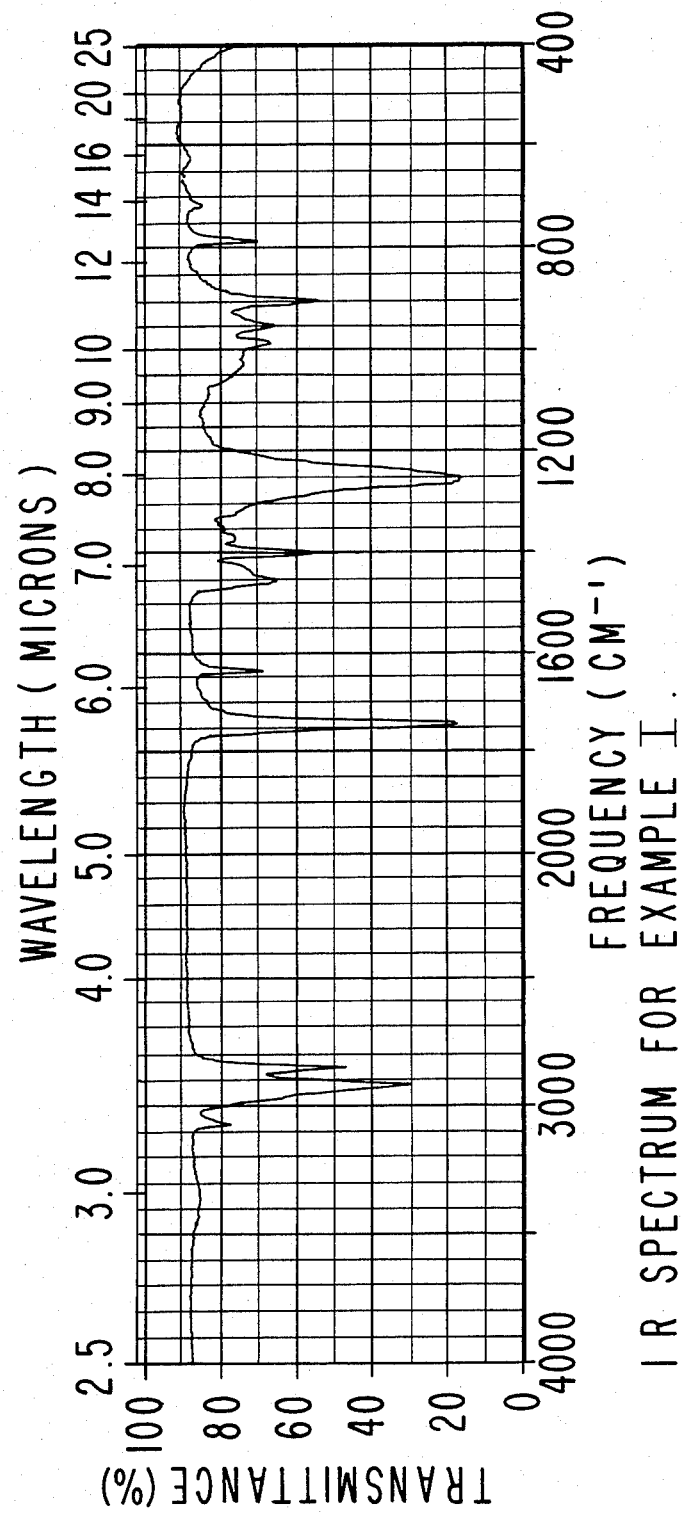

FIG. 2 is the infra-red spectrum for the compound having the structure:

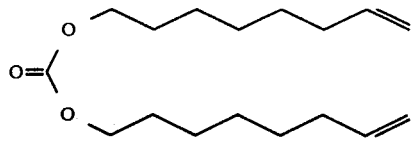

produced according to Example I (bulked distillation fractions 3-11).

Figure 3:
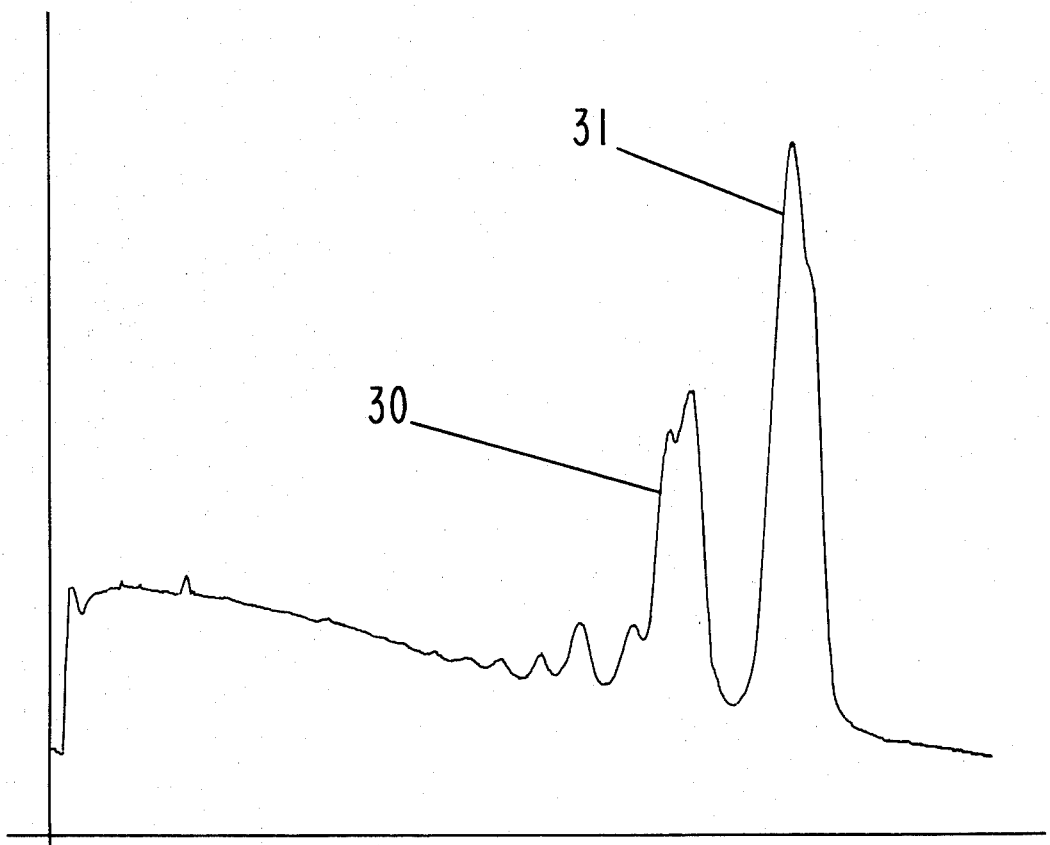

FIG. 3 is the GLC profile for the first distillation product of the reaction product of Example II containing the compound having the structure:

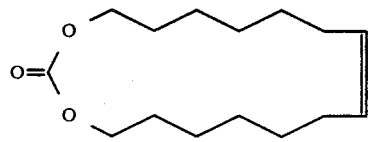

(cis and trans isomers). (Conditions: 10% carbowax column programmed at 80°-220° C. at 8° C. per minute).

Figure 4:
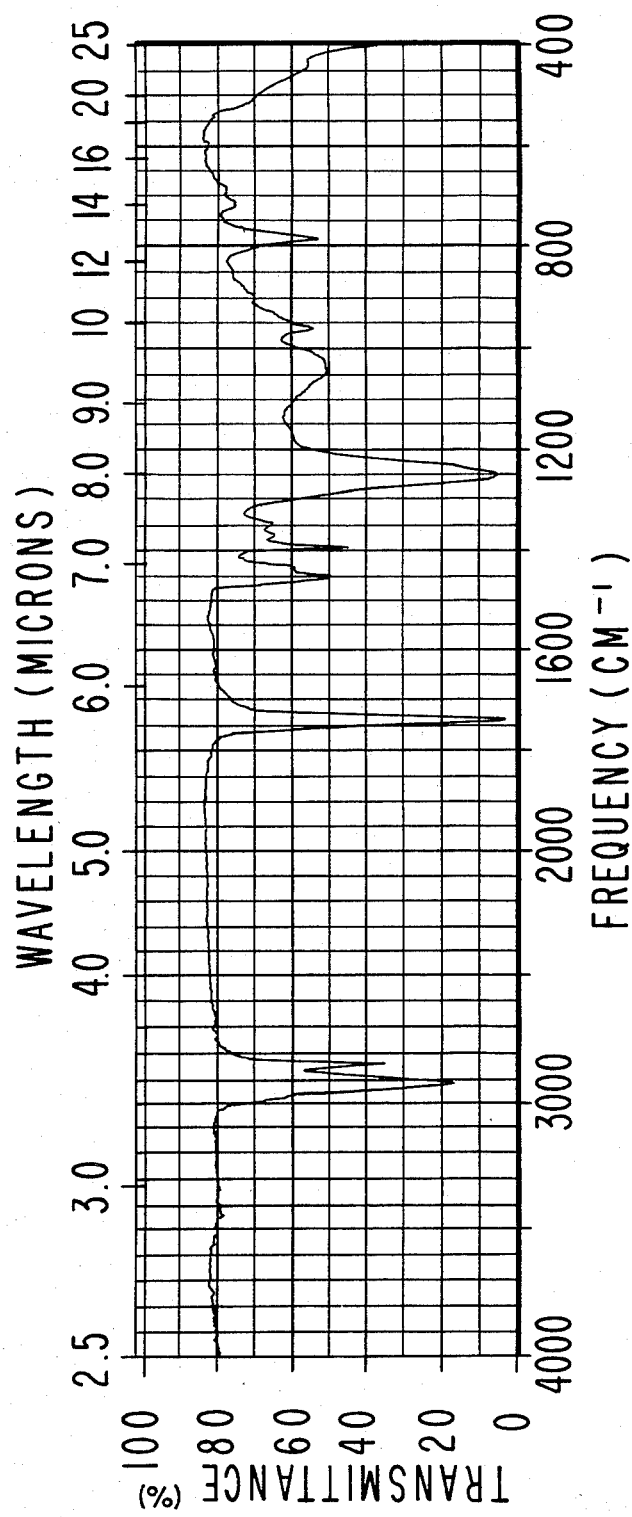

FIG. 4 is the infra-red spectrum for the peak indicated by reference numeral "31" of the GLC profile of FIG. 3 having the structure:

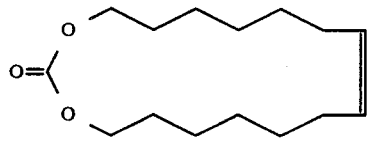

Figure 5:
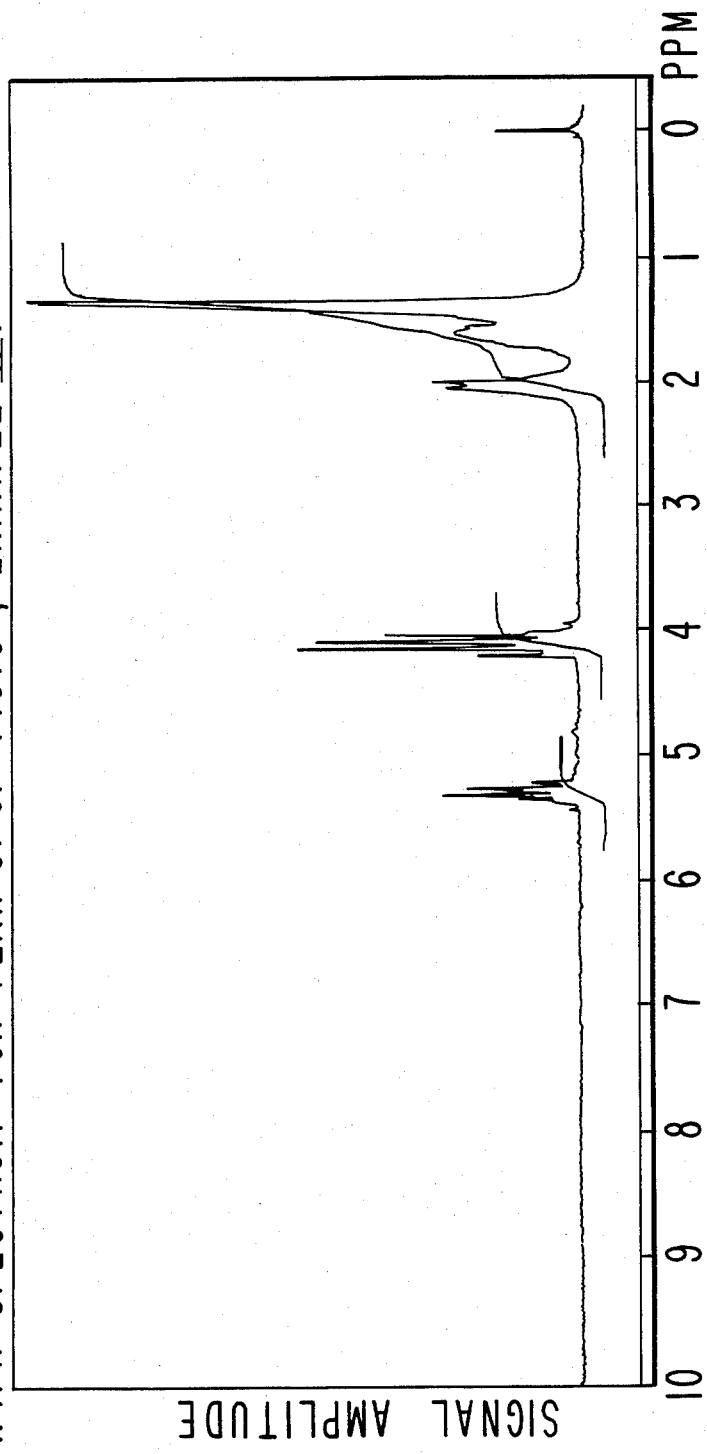

FIG. 5 is the NMR spectrum for the peak indicated by reference numeral "31" on the GLC profile of FIG. 3 for the compound having the structure:

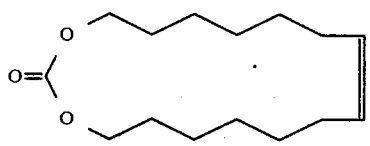

(cis and trans isomers). (Conditions: Field strength: 100 MHz; Solvent: $CFCl_3$).

Figure 6:
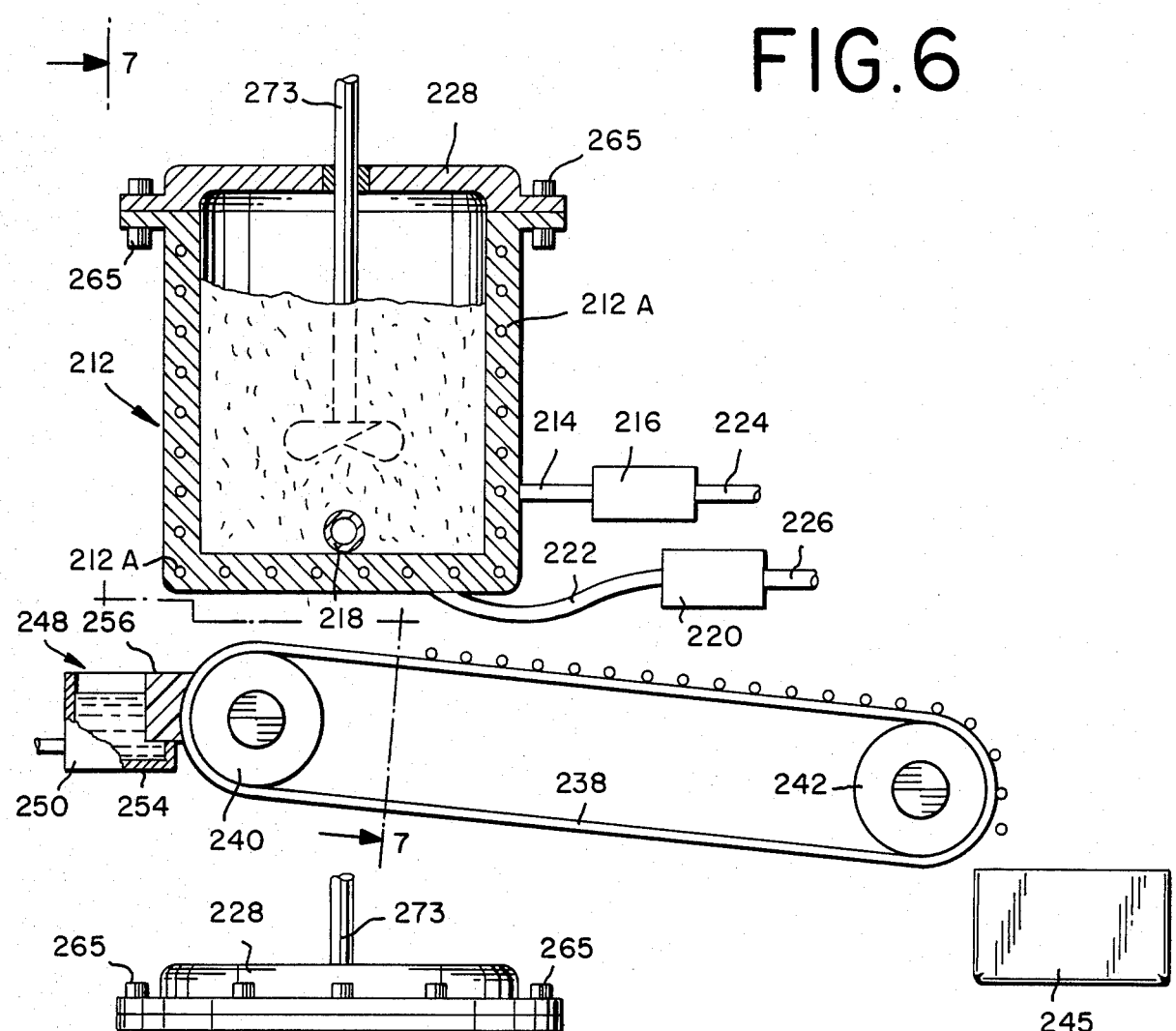

FIG. 6 is a partial side elevation and partial sectional view of an apparatus for forming scented polymer using at least one of the compounds defined according to the generic structure:

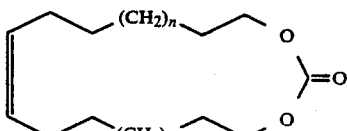

wherein n and m are each the same or different and each represents integers of from 1 up to 8.

Figure 7:
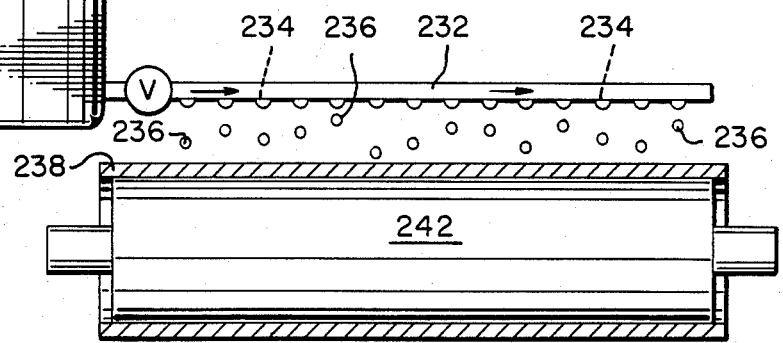

FIG. 7 is a section taken on line 7—7 of FIG. 6.

DETAILED DESCRIPTION OF THE DRAWINGS

FIG. 3 is the GLC profile for the first distillation product of the reaction product of Example II (conditions: 10% Carbowax column programmed at 80°-220° C. at 8° C. per minute). The peak indicated by reference numeral "30" is the peak for the starting material produced according to Example I having the structure:

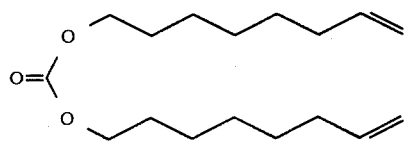

The peak indicated by reference numeral "31" is the peak representing "cis" and "trans" isomers of the compound having the structure:

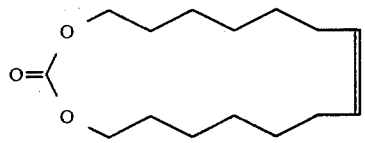

Referring to the drawings in FIGS. 6 and 7 in particular, the invention embodied therein comprises a device for forming scented polymer pellets (e.g. polyethylene, polypropylene or mixtures of polyepsilon caprolactone and polyethylene or polypropylene or co-polymers of polyvinyl acetate and polyethylene or the like) which comprises a vat or container 210 into which a mixture of polymers such as polyethylene and at least one of the cis or trans isomers or a mixture of cis and trans isomers of the compound having the structure:

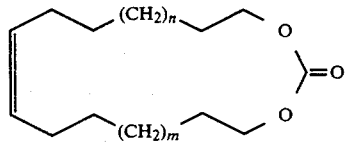

wherein n and m are each the same or different and each represents integers of from 1 up to 8 or a mixture of perfume materials including as a key ingredient one or both of the isomers defined according to the structure:

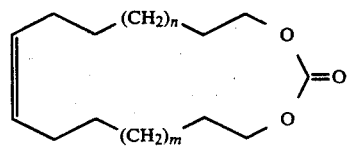

wherein n and m are each the same or different and each represents integers of from 1 up to 8, is placed.

The container is closed by an air-tight lid 228 clamped to the container by clamps 265. A stirrer 273 traverses the lid or cover 228 in air-tight manner and is rotated in a suitable manner. A surrounding cylinder 212 having heating coils which are supplied with electrical current through cable 214 from a rheostat or control 216 is operated to maintain the temperature inside the container 210 such that the polymer such as polyethylene in the container will be maintained in a molten or liquid state. It has been found advantageous to employ a colorless, odorless polymer such as low density polyethylene with a viscosity ranging between 180 and 220 centistokes and having a melting point in the neighborhood of 220° F. The heater 212 is operated to maintain the upper portion of the container 210 within a temperature range of from 250°-350° F. An additional bottom heater 218 is regulated through a control 220 connected thereto through a connecting wire 222 to maintain the lower portion of the container 210 within a temperature range of from 250° to 350° F.

In accordance with this aspect of the invention, a polymer such a polyethylene or polypropylene is added to the container 210 and is then heated from 10 to 12 hours whereafter a scent or aroma imparting material containing at least one of the isomers of the compound having the structure:

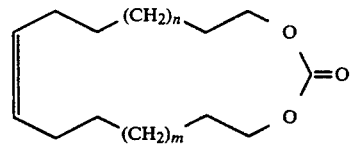

wherein n and m are each the same or different and each represents integers of from 1 up to 8 is quickly added to the melt. The material must be compatible with the polymer and forms a homogeneous liquid melt therewith. The heat resisting mixture generally containing about 10-40% by weight of material having the structure:

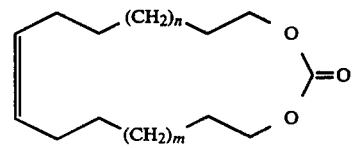

wherein n and m are each the same or different and each represents integers of from 1 up to 8 or mixture containing such compound or isomer is added to the polymer.

After the compound (or cis or trans isomer thereof) having the structure:

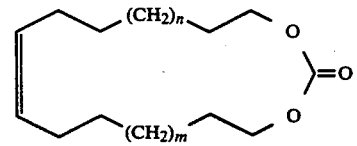

wherein n and m are each the same or different and each represents integers of from 1 up to 8 is added to container 210, the mixture is stirred for a few minutes, for example 5-15 minutes, and maintained within the temperature range as indicated previously by the heating coils 212 and 218 respectively. The controls 216 and 220 are connected through cables 224 and 226 to a suitable supply of electric current for supplying the power for heating purposes.

Thereafter the valve "V" is opened permitting the mass to flow outwardly through a conduit 232 having a multiplicity of orifices 234 adjacent the lower side thereof. The outer end of the conduit 232 is closed so that the liquid polymer and substance containing at least one of the isomers having the structure:

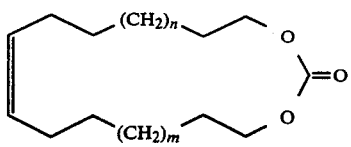

wherein n and m are each the same or different and each represents integers of from 1 up to 8 will continuously drop through the orifice 234 downwardly from the conduit 232. During this time the temperature of the polymer and at least one of the isomers having the structure:

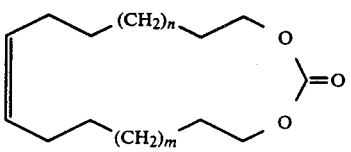

wherein n and m are each the same or different and each represents integers of from 1 up to 8 in the container 210 is accurately controlled so that a temperature in the range of from 210° up to 275° F. will be maintained in the material exiting in the conduit 232. The regulation of the temperature through the control 216 and the control 220 is essential in order to insure temperature balance to provide for the continuous dropping or dripping of the molten polymer and the material having the structure:

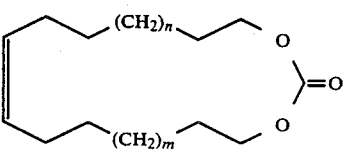

wherein n and m are each the same or different and each represents integers of from 1 up to 8, or mixture containing same through the orifices 234 at a range which will insure the formation of droplets 236 which will fall downwardly onto a moving conveyor belt 238 trained to run between conveyor wheels 240 and 242 beneath the conduit 232. When the droplets 236 fall onto the conveyor belt 238 they form pellets 244 which harden almost instantaneously and fall off the end of the conveyor 238 into a container 246 which is advantageously filled with water or some other suitable liquid to insure the rapid cooling of each of the pellets. The pellets 244 are then collected from the container 246 and packaged for shipment.

A feature of the invention is the provision for moistening the conveyor belt 238 to insure the rapid formation of the solid polymer scented pellets 244 without sticking to the belt. The belt 238 is advantageously of a material which will not normally stick to a melted polymer but the moistening means 248 insures a sufficiently cold temperature of the belt surface for the adequate formation of the pellets 244. The moistening means comprises a container 250 which is continuously fed with water 252 to maintain a level 254 for moistening a sponge element 256 which bears against the exterior surface of the belt 238.

THE INVENTION

It has now been discovered that novel solid and liquid foodstuff, chewing gum, medicinal products and flavoring compositions having pear, peach, tropical fruit (e.g. mango) and blackberry flavors with sweet, musky aroma characteristics and sweet and musky flavor characteristics, and novel perfume compositions and perfumed articles having sweet, musky aromas may be provided by the macrocyclic carbonates defined according to the generic structure:

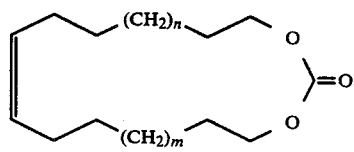

wherein n and m are each the same or different and each represents integers of from 1 up to 8.

The macrocyclic carbonates of our invention may be prepared by first reacting an unsaturated alcohol having the structure:

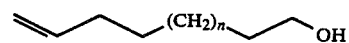

or mixture of unsaturated alcohols having the structures:

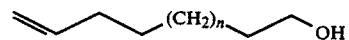

and

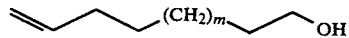

with a dialkyl carbonate having the structure:

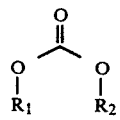

wherein $R_1$ and $R_2$ are the same or different $C_1$–$C_4$ lower alkyl in the presence of an alkali metal alkoxide having the formula MOR" according to the reaction:

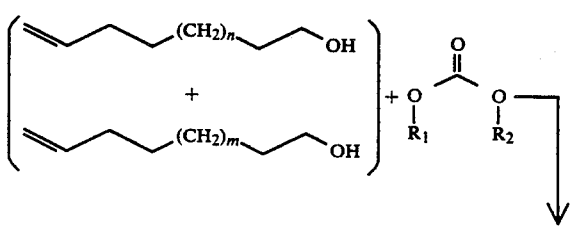

-continued

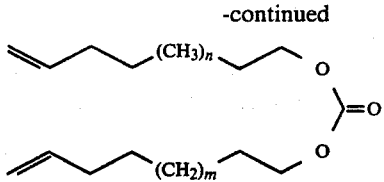

thereby forming the genus of novel intermediates defined according to the structure:

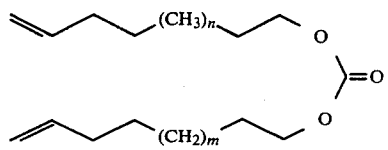

wherein M represents alkali metal such as sodium, potassium and lithium and wherein R" represents lower alkyl such as methyl, ethyl, propyl, n-butyl and tertiary butyl. In terms of the alkali metal alkoxide, other metal alkoxides may be used, e.g. aluminum triisopropylate. Examples of alkali metal alkoxides and other metal alkoxides, accordingly, are specifically, sodium methoxide, sodium ethoxide, sodium t-butoxide, potassium methoxide, potassium ethoxide, potassium t-butoxide and aluminum triisopropylate. The reaction between the omega alcohol and the dialkyl carbonate takes place in the presence of a solvent inert to the reactants such as toluene, xylene and the like. The solvent must have such physical properties as to be (a) unreactive with the reactants or reaction products and (b) have a boiling point whereby the reaction mass may be refluxed at a temperature convenient to cause the reaction to take place in a reasonable period of time, e.g. from about 1 up to about 10 hours.

The mole ratio range of dialkyl carbonate:omega alcohol may vary from about 3 moles dialkyl carbonate:0.5 moles omega alcohol down to 1 mole dialkyl carbonate:2 moles omega alcohol. It is preferred that the mole ratio of dialkyl carbonate:omega alcohol be about 2:1. The molar concentration in the reaction mass of the metal alkoxide catalyst may vary from about 0.005 moles per liter up to about 0.01 moles per liter with a molar concentration of about 0.05 being preferred.

The reaction temperature range may vary from about 100° C. up to about 150° C. and the reaction pressure may vary from about 0.5 atmospheres up to about 10 atmospheres with 1 atmosphere pressure being most convenient. Higher temperatures of reaction necessitate higher pressures over the reaction mass in order to prevent the reaction product from evaporating therefrom.

At the end of the reaction, the reaction product may be purified according to standard procedures such as fractional distillation for use in the subsequent reaction.

The second "metathesis" reaction is carried out on the resulting carbonate derivative defined according to the structure:

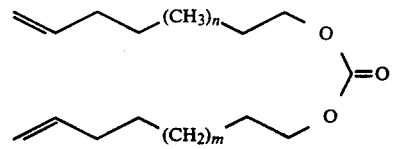

whereby 1 mole of ethylene is split out of the reaction product according to the reaction:

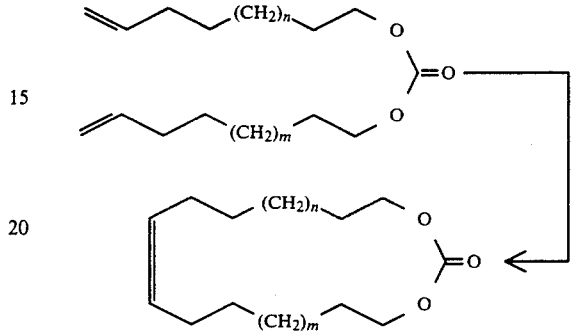

wherein n and m are the same or different and each represents integers of from 1 to 8. The conditions for this metathesis reaction are set forth in one of the following papers, the disclosures of which are incorporated by reference herein:

(i) Van Dam et al "Homogeneous Catalytic Metathesis of Unsaturated Fatty Esters: New Synthetic Method for Preparation of Unsaturated Mono- and Dicarboxylic Acids", Volume 51, Journal of the American Oil Chemists' Society, pages 389–392, 1974.

(ii) Mol, "Metathesis of functionalized olefins" Chemtech, April 1983, pages 250–255.

(iii) Otton, et al "Metathesis of Functionalized Olefins: Homogeneous Cross-Metathesis of Cycloolefin and Ethylenic Esters", Journal of Molecular Catalysis, 8(1980), pages 313–324.

(iv) Tsuji and Hashiguchi, "Metathesis Reactions of Unsaturated Esters Catalyzed by Homogeneous Tungsten Complexes, Syntheses of Civetone and Macrolides", Journal of Organometallic Chemistry, 218(1981), pages 69–80.

(v) Villemin, "Synthesis of Macrolides by metathesis", Tetrahedron Letters, Vol. 21, 1980, pages 1715–1718.

Thus, the foregoing metathesis reaction may be carried out using as primary catalysts, for example, $WCl_6$ and $WOCl_4$, and as co-catalysts, tetramethyl tin, tetramethyl lead, $Cp_2Ti(CH_3)_2$ and $Cp_2Zr(CH_3)_2$.. The catalyst system $WOCl_4/Cp_2Ti(CH_3)_2$ and $WCl_6$/tetramethyl tin are most preferred. The metathesis reaction is carried out in a solvent as indicated in the above references incorporated herein by reference such as chlorobenzene and the like. The metathesis reaction is carried out at a temperature in the range of from about 80° C. up to about 120° C. at from about atmospheric pressure up to about 4 atmospheres over a period of time of from about 1 hour up to about 12 hours. Higher temperatures of reaction give rise to shorter periods of times of reaction. Higher temperatures of reaction necessitate higher pressures of reaction.

The weight ratio of catalyst:carbonate ester reactant may vary from about 1:20 up to about 1:5 with a preferred weight ratio of 1:10. The concentration of catalyst in the reaction mass may vary from about 2 grams per liter up to about 12 grams per liter with a preferred concentration of catalyst in the reaction mass of about 5–6 grams per liter.

When the macrocyclic carbonates of our invention are used as food flavor adjuvants, the nature of the co-ingredients included with said macrocyclic carbonates in formulating the product composition will serve to alter the organoleptic characteristics of the ultimate foodstuff treated therewith.

As used herein in regard to flavors, the terms "alter" and "modify" in their various forms mean "supplying or imparting flavor character or note to otherwise bland, relatively tasteless substances or augmenting the existing flavor characteristic where a natural flavor or synthetic flavor or mixture of natural and synthetic flavors is deficient in some regard, or supplementing the existing flavor impression to modify its quality, character or taste".

As used herein, the term "enhance" is intended to mean the intensification (without effecting a change in kind of quality or aroma or taste) of one or more taste and/or aroma nuances present in the organoleptic impression of a consumable material, e.g., foodstuff, tobacco, chewing gum, medicinal product, perfume composition or perfumed article.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

As used herein, the term "chewing gum" is intended to mean a composition which comprises a substantially water-insoluble, chewable plastic gum base such as chicle, or substitutes therefor, including jelutung, guttakay rubber and/or certain comestible natural or synthetic resins or waxes. Incorporated within the gum base, in admixture therewith may be plasticizers or softening agents, e.g., glycerine; and a flavoring composition which incorporates the macrocyclic carbonates of our invention, and, in addition, sweetening agents which may be sugars, including sucrose or dextrose and/or artificial sweeteners including dipeptides, cyclamates and saccharin. Other optional ingredients may also be present.

The term "medicinal product" includes both solids and liquids which are ingestible, non-toxic materials having medicinal value such as cough syrups, cough drops, toothpaste, aspirin and chewable medicinal tablets as further exemplified herein.

Substances suitable for use herein as co-ingredients or flavoring adjuvants are well known in the art for such use being extensively described in the relevant literature. Such material is required to be "ingestibly" acceptable and thus non-toxic or otherwise non-deleterious. Particularly critical is the additional requirement that such material be organoleptically compatible with the macrocyclic carbonates encompassed within the scope of our invention. Also critical is the additional requirement that such material be nonreactive (within the range of storage conditions and room temperature use conditions) with macrocyclic carbonates.

Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxy toluene, (2,6-di-tertiary-butyl-4-methyl phenol), propyl gallate and the like and sequestrants, e.g., citric acid.

Thickener compounds include carriers, binders, protective colloids, suspending agents, emulsifiers, and the like, e.g., agaragar, carrageenan; cellulose and cellulose derivatives such as carboxymethyl cellulose and methyl cellulose; natural and synthetic gums such as gum arabic, gum tragacanth; gelatin, proteinaceous materials; lipids, carbohydrates, starches, pectins, and emulsifiers, e.g., mono- and diglycerides of fatty acids, skim silk powder, hexoses, pentoses, disaccharides, e.g., sucrose, corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents, such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, turmeric and curcuma and the like, firming agents such as aluminum sodium sulfate, calcium chloride and calcium gluconate; texturizers, anti-caking agents, e.g., aliminum calcium sulfate and tribasic calcium phosphate; enzymes, yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, cis and trans 2-methyl-2-pentenoic acid, and cis and trans 2-methyl-3-pentenoic acid; ketones and aldehydes, e.g., acetaldehyde, acetophenone, acetone, acetyl methyl carbinol, acrolein, n-butanal, crotonal, diacetyl, beta, beta-dimethyl-acrolein, n-hexanal, 2-hexenal, cis-3-hexenal, 2-heptenal, 4-(p-hydroxyphenyl)-2-butanone, alpha-ionone, beta-ionone, methyl-3-butanone, 2-pentanone, 2-pentenal and propanal; alcohols such as 1-butanol, benzyl alcohol, 1-borneol, trans-3-buten-1-ol, ethanol, geraniol, 1-hexanol, 2-heptenol-1, trans-3-hexenol-1, cis-3-hexen-1-ol, 3-methyl-3-buten-1-ol, 1-penten-2-ol, 1-penten-3-ol, p-hydroxyphenyl-2-ethanol, isoamyl alcohol, isofenchyl alcohol, phenyl-2-ethanol, alpha-terpineol, cis-terpineol hydrate; esters, such as butyl acetate, ethyl acetate, ethyl acetoacetate, ethyl benzoate, ethyl butyrate, ethyl caproate, ethyl cinnamate, ethyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, n-hexyl butyrate, isoamyl acetate, isopropyl butyrate, methyl acetate, methyl-n-butyrate, methyl caproate, methyl isobutyrate, alpha-methyl-n-butyrate, n-propyl acetate, n-amyl acetate, n-amyl-n-butyrate, benzyl salicylate, dimethyl anthranilate, ethyl methylphenylglycidate, ethyl succinate, isobutyl cinnamate, and terpenyl acetate; lactones, such as delta-decalactone, delta-undecalactone, delta-nonyl-lactone, gamma-undecalactone, gamma-dodecalactone and gamma nonyl-lactone as well as "peach" lactones; essential oils, such as jasmine absolute, rose absolute, orris absolute, lemon essential oil, Bulgarian rose, yara yara, natural raspberry oil and vanilla; sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff whether simulated or natural, and should, in any event, be capable of providing an environment in which the macrocyclic carbonates can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of macrocyclic carbonates employed in a particular instance can vary over a relatively wide range whereby specific desired organoleptic effects (having particular reference to the nature of the product) are achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to alter, modify, or enhance the organoleptic characteristics of the parent composition, whether foodstuff per se or flavoring composition.

The use of insufficient quantities of the macrocyclic carbonates will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it has been found that quantities of macrocyclic carbonates ranging from a small but effective amount, e.g., 0.0001 parts per million up to about 50 parts per million by weight based on total composition are suitable. Concentrations in excess of the maximum quantity stated are not normally recommended, since they fail to provide commensurate enhancement or augmentation of organoleptic properties. In those instances wherein the macrocyclic carbonates are added to the foodstuff as an integral component of a flavoring composition, it is, of course, essential that the total quantity of flavoring composition employed be sufficient to yield an effective concentration (of macrocyclic carbonates) in the foodstuff product.

Food flavoring compositions prepared in accordance with the present invention preferably contain the macrocyclic carbonates in concentrations ranging from about 0.01% up to about 15% by weight based on the total weight of the said flavoring composition.

The compositions described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the macrocyclic carbonates with, for example, gum arabic, gum tragacanth, carrageenan and the like, and thereafter spray-drying the resultant mixture whereby to obtain the particulate solid product. Pre-prepared flavor mixes in powder form, e.g., a fruit-flavored powder mix are obtained by mixing the dried solid components, e.g., starch, sugar and the like and the macrocyclic carbonates in a dry blender until the requisite degree of uniformity is achieved.

It is presently preferred to combine with the macrocyclic carbonates the following adjuvants:
p-Hydroxybenzyl acetone;
Geraniol;
Acetaldehyde;
Maltol;
Ethyl methyl phenyl glycidate;
Benzyl acetate;
Dimethyl sulfide;
Vanillin;
Methyl cinnamate;
Ethyl pelargonate;
Methyl anthranilate;
Isoamyl acetate;
Isobutyl acetate;
Alpha ionone;
β-Damascone;
β-Damascenone;
Ethyl butyrate;
Acetic acid;
n-Hexyl acetate;
n-Hexyl isobutyrate;
Trans-2-hexenal;
Linalyl isobutyrate;
n-Hexyl-2-methyl-n-butyrate;
Gamma-undecalactone;
Gamma-nonalactone;
Gamma decalactone;
Delta undecalactone;
Delta dodecalactone;
Delta nonyl lactone;
"Peach" lactone;
Naphthyl ethyl ether;
Diacetyl;
Apple Fusel Oil;
Sauge Sclaree;
Coriander Oil;
Ethyl acetate;
Anethole;
Isoamyl-n-butyrate;
Ethyl-2-methyl-cis-3-pentenoate;
Cis-3-hexenol-1;
2-Methyl-cis-3-pentenoic acid;
2-Methyl-2-pentenoic acid;
Elemecine (4-allyl-1,2,6-trimethoxy benzene);
Isoelemecine (4-propenyl-1,2,6-trimethoxy benzene);

2-(4-hydroxy-4-methylpentyl) norbornadiene prepared according to U.S. Pat. No. 3,886,289; and 2- and 3-cyclotetradecen-1-ones of U.S. Pat. No. 4,282,274.

The macrocyclic carbonates and one or more auxiliary perfume ingredients including, for example, alcohols, aldehydes, nitriles, esters, cyclic esters other than the macrocyclic carbonates of our invention, ketones, natural essential oils and synthetic essential oils may be admixed so that the combined odors of the individual components produce a pleasant and desired fragrance, particularly and preferably in musk and "animal-like" fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to its particular olfactory characteristics, but the overall effect of the perfume composition will be the sum of the effects of each of the ingredients. Thus, the macrocyclic carbonates can be used to alter the aroma characteristics of a perfume composition, for example, by utilizing or moderating the olfactory reaction contributed by at least one other ingredient in the composition.

The amount of macrocyclic carbonates of our invention which will be effective in perfume compositions depends on many factors including the other ingredients, their amounts and the effects which are desired. It has been found that perfume compositions containing as little as 0.01% of the macrocyclic carbonates and even less (e.g. 0.005%) can be used to impart rich sweet, musky notes to soaps, anionic, cationic, nonionic and zwitterionic detergents, fabric softener articles, cosmetics, perfumed polymers, and other perfumed articles. The amount employed can range up to 50% of the fragrance components and will depend on considerations of cost, nature of the end product, the effect desired on the finished product and the particular fragrance sought.

The macrocyclic carbonates of our invention are useful taken alone or in perfume compositions as olfactory components in anionic, cationic, nonionic and zwitterionic detergents, soaps, fabric softener compositions, fabric softener articles for use in clothes driers (e.g. BOUNCE ® a registered trademark of the Procter & Gamble Company of Cincinnati, Ohio), space odorants and deodorants, perfumes, colognes, toilet water, bath preparations such as bath oils and bath solids; hair preparations such as lacquers, brilliantines, creams, deodorants, hand lotions and sun screens; powders such as talcs, dusting powders, face powders, and perfumed polymers and the like. When used as an olfactory component in perfume compositions or perfumed articles such as anionic, cationic, nonionic or zwitterionic detergents and in fabric softener compositions and fabric softener articles (e.g. for use in clothes driers), as little as 0.05% of the macrocyclic cabonates of our invention will suffice to impart an intense sweet, musky fragrance. Generally no more than 5% of the macrocyclic carbonates of our invention based on the ultimate perfumed article end product is required. Accordingly, the perfumed articles of our invention can contain from about 0.05% up to about 5% by weight of the macrocyclic carbonates of our invention.

In addition, the perfume composition or fragrance composition of our invention or the macrocyclic carbonates of our invention can contain a vehicle or carrier. The vehicle can be a liquid such as a non-toxic alcohol such as ethanol or a non-toxic glycol such as propylene glycol or the like. The carrier can also be an absorbent solid such as a gum (e.g. gum arabic, guar gum or xanthan gum) or components for encapsulating the composition (such as gelatin as by means of coacervation, or such as a urea formaldehyde prepolymer for forming a urea formaldehyde polymeric wall around a liquid perfume center).

More specifically, the macrocyclic carbonates of our invention may be blended into polymers when forming perfumed polymers by means of extrusion using a single or double screw extruder or technique such as that set forth in U.S. Pat. No. 4,247,498 issued on Jan. 27, 1981 the disclosure for which is incorporated by reference herein, which discloses microporous polymers which are capable of containing volatile substances such as perfumes and the like and forms ranging from films to blocks and intricate shapes from synthetic themoplastic polymers such as olefinic condensation or oxidation polymers.

Other techniques of blending the macrocyclic carbonates of our invention with polymers are exemplified in U.S. Pat. No. 3,505,432 (the specification for which is incorporated by reference herein) which discloses a method for scenting a polyolefin with such materials as the macrocyclic carbonates of our invention which comprises:

(a) mixing a first amount of the liquid polyolefin (e.g. polyethylene or polypropylene) with a relatively large amount of scent-imparting material (in this case one or more of the macrocyclic carbonates of our invention) to form a flowable mass;

(b) forming drops of said mass and causing substantially instantaneous solidification of said drops into polyolefin pellets having a relatively large amount of such scent-imparting materials as the macrocyclic carbonates of our invention, imprisoned therein;

(c) melting said pellets with a second amount of polyolefin and said second amount being larger than the first amount; and (d) solidifying the melt of (c).

The following Examples I and II set forth techniques for preparing the macrocyclic carbonates of our invention. Examples III et seq. set forth organoleptic uses of the macrocyclic carbonates of our invention.

All parts and percentages given herein are by weight unless otherwise specified.

EXAMPLE I

Preparation of Di(7-octenyl)carbonate

Reaction:

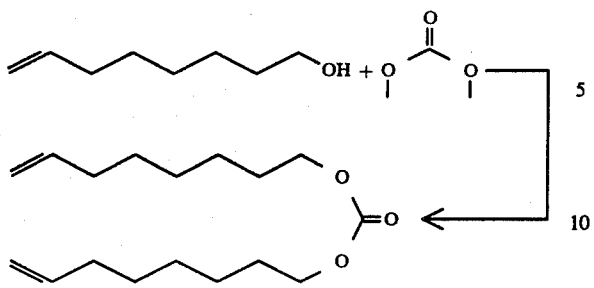

Into a 1 liter flask equipped with reflux condenser, thermometer, stirrer and heating mantle are placed the following materials:

dimethyl carbonate—90 grams (1 mole)
sodium methoxide—5 grams
octenol-1—256 grams
toluene (anhydrous)—150 grams The resulting mixture is heated to reflux and methanol reaction product is distilled off (via a Vigreux column and reflux head) until the vapor temperature remains at 110° C. and the liquid temperature remains at 135°–140° C. (time approximately 5 hours).

The reaction mass is cooled and 60 grams of acetic acid and 100 grams of water and 150 grams of crushed ice are added to the reaction mass.

The reaction mass is stirred for a period of 30 minutes and placed in a separatory funnel. The aqueous layer is extracted with toluene and the toluene extracts are combined with the organic phase. The organic phase is then washed as follows:

(i) three 200 ml volumes of water;
(ii) twice with water to a pH of 4.5;
(iii) three times with water to a pH of 6.

The toluene is stripped from the reaction mass and the reaction mass is distilled on a 14″ Vigreux column to yield the following fractions:

| Fraction Number | Vapor Temp. (°C.) | Liquid Temp. (°C.) | Vacuum mm/Hg | Weight of Fraction (grams) |
|---|---|---|---|---|
| 1 | 88 | 157 | 3.0 | 21.9 |
| 2 | 150 | 176 | 2.5 | 22.7 |
| 3 | 150 | 176 | 2.5 | 11.1 |
| 4 | 150 | 176 | 2.5 | 15.3 |
| 5 | 150 | 176 | 2.5 | 11.9 |
| 6 | 152 | 176 | 2.5 | 33.6 |
| 7 | 153 | 177 | 2.6 | 39.4 |
| 8 | 154 | 178 | 2.8 | 34.4 |
| 9 | 151 | 179 | 2.4 | 16.2 |
| 10 | 151 | 179 | 2.5 | 21.6 |
| 11 | 154 | 190 | 2.4 | 26.1 |
| 12 | 158 | 229 | 2.4 | 8.8 |

Fractions 3–11 are bulked for subsequent reaction.

Figure 1:
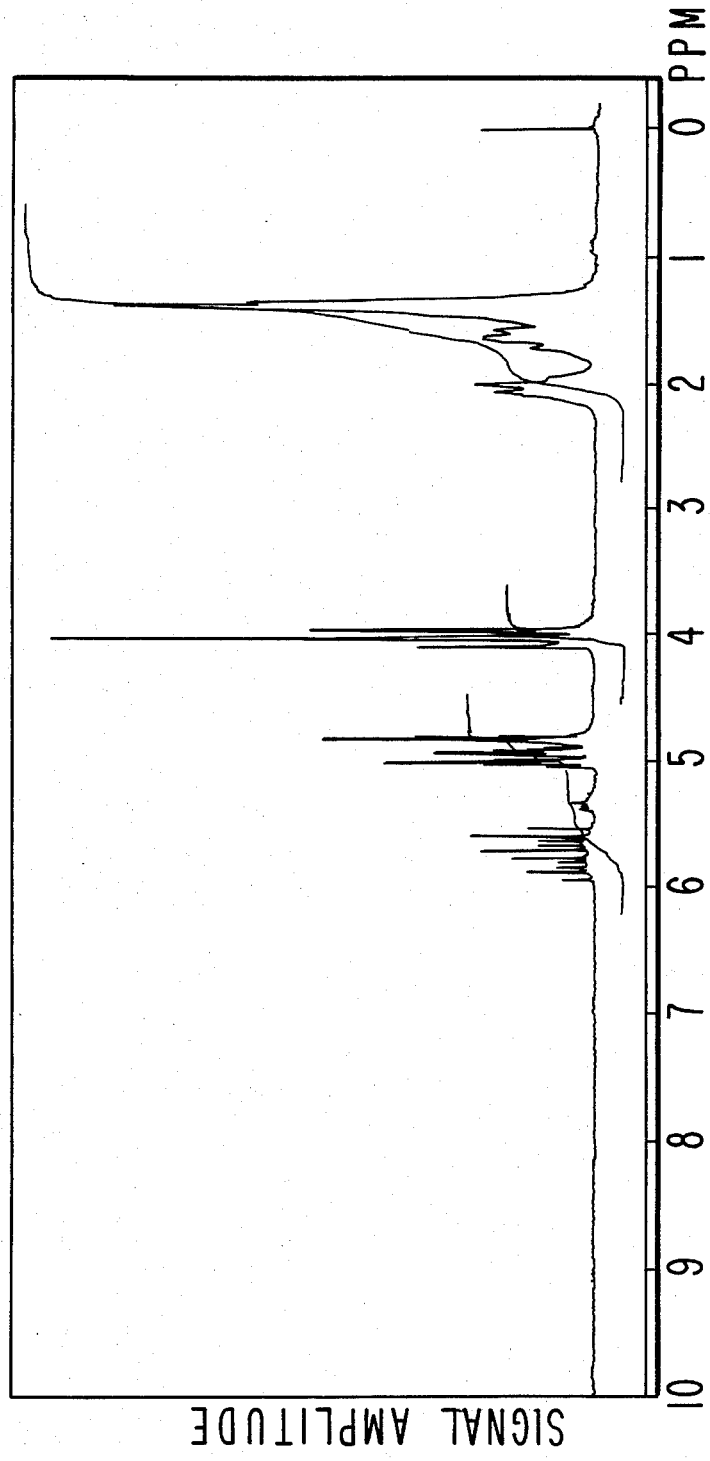
FIG. 1 is the NMR spectrum for the compound having the structure.

FIG. 1 is the NMR spectrum for the reaction product having the structure:

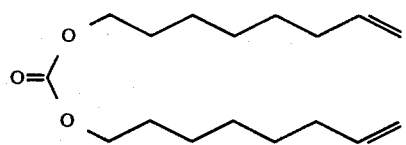

(conditions: Field Strength: 100 MHz; Solvent: CFCl$_3$).

FIG. 2 is the infra-red spectrum for the reaction product having the structure:

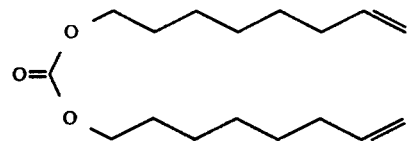

EXAMPLE II

Preparation of 1,3-Dioxacycloheptadec-10-en-2-one

Reaction:

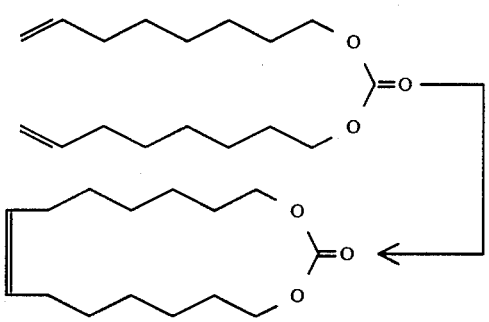

Into a 1 liter flask equipped with reflux condenser, thermometer, heating mantle and stirrer is placed 100 ml anhydrous monochlorobenzene. To the anhydrous monochlorobenzene slowly is added 386.6 mg of tungsten hexachloride (WCl$_6$). The resulting mixture is stirred for a period of 15 minutes. Under a nitrogen blanket is added the compound produced according to Example I (5.9 grams) having the structure:

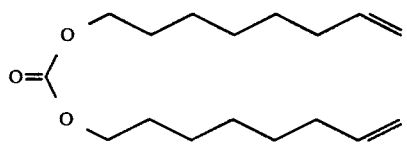

The reaction mass is stirred for 1 hour at 40° C. and 425 microliters of tetramethyl tin is added to the reaction mass. The reaction mass is stirred for a period of 15 minutes.

The resulting mixture is then added to 200 ml chlorobenzene and the resulting mixture is heated to 90° C. over a period of 3 hours and aged for another 7 hour period.

At this point in time GLC analysis indicates 55% conversion.

Conversion is raised to 65% by adding to the reaction mass an additional 350 microliters of tetramethyl tin and heating to 85° C. and adding dropwise over a 3.5 hour period, 300 mg of tungsten hexachloride dissolved in 100 ml chlorobenzene and then aging for 7 hours.

The reaction mass is then mixed with 370 ml water and stirred for a period of 30 minutes. The organic phase is then washed twice with water and the solvent is stripped off leaving 6.01 grams of product. This product is distilled at 0.5 mm/Hg and 130°–180° C. The weight of distillate is 1.7 grams.

FIG. 3 is the GLC profile of this distillation product (conditions: 10% Carbowax column programmed at 80°–220° C. at 8° C. per minute).

The peak indicated by reference numeral "30" is the peak for the starting material having the structure:

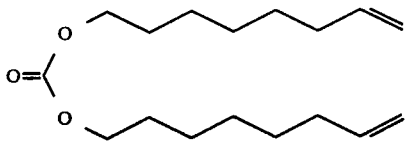

The peak indicated by reference numeral "31" is the peak for the resulting product having the structure:

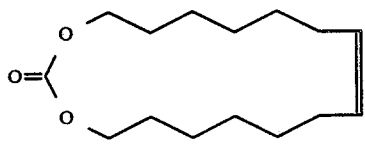

The GLC peaks are then further chromatographed to yield the compound having the structure:

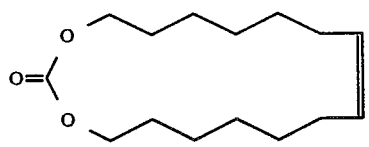

FIG. 4 is the infra-red spectrum for the peak indicated by reference numeral "31" of the GLC profile of FIG. 3 having the structure:

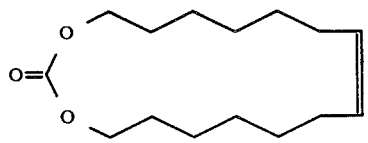

FIG. 5 is the NMR spectrum for the peak indicated by reference numeral "31" of the GLC profile of FIG. 3 having the structure:

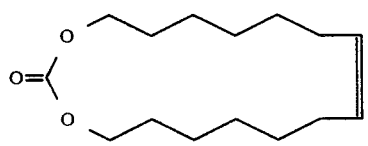

(conditions: Field Strength: 100 MHz; Solvent: CFCl$_3$).

The compound produced in this manner having the structure:

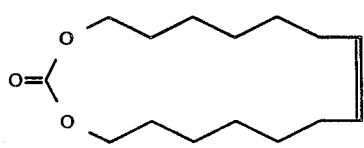

is used in subsequent Examples III, et seq.

EXAMPLE III

Musk Perfume Formulation

The following musk perfume formulation is prepared:

| Ingredients | Parts by Weight |
|---|---|
| Musk ambrette | 200 |
| Musk ketone | 200 |
| Beta ionone | 50 |
| Vetiveryl acetate | 50 |
| Sandalwood oil | 100 |
| Benzyl benzoate | 400 |
| Mixture of cis and trans isomers having structures: 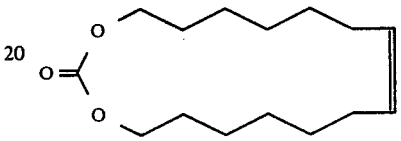 (50:50 cis:trans mixture) | 20 |

The mixture of compounds having the structure:

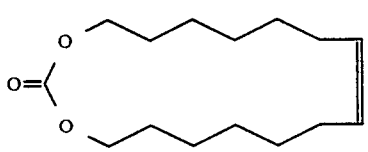

imparts to this musk formulation a natural "animal musk" and sweet aroma causing it to be more "natural like". Accordingly, this formulation can be described as "musky with animal-like and sweet undertones".

EXAMPLE IV

Preparation of Cosmetic Powder Compositions

Cosmetic powder compositions are prepared by mixing in a ball mill 100 grams of talcum powder with a 0.25 grams of each of the substances set forth in Table I below. Each of the cosmetic powder compositions has an excellent aroma as described in Table I below:

TABLE I

| Substance | Aroma Description |
|---|---|
| 50:50 mixture of cis and trans isomers having the structure: | A sweet, musky aroma. |
| Perfume composition of Example III. | Musky with animal-like and sweet undertones. |
| Cis isomer of compound having the structure: | A sweet musky aroma. |

TABLE I-continued

| Substance | Aroma Description |
|---|---|
| Trans isomer of compound having the structure: [structure shown with O, O, and long hydrocarbon chains] | A sweet musky aroma. |

EXAMPLE V

Perfumed Liquid Detergents

Concentrated liquid detergents (lysine salt of n-dodecylbenzene sulfonic acid as more specifically described in U.S. Pat. No. 3,948,818 issued on Apr. 6, 1976 incorporated by reference herein) with aroma nuances as set forth in Table I of Example IV, are prepared containing 0.10%, 0.15%, 0.20%, 0.25%, 0.30% and 0.35% of the substance set forth in Table I of Example IV. They are prepared by adding and homogeneously mixing the appropriate quantity of substance set forth in Table I of Example IV in the liquid detergent. The detergents all possess excellent aromas as set forth in Table I of Example IV, the intensity increasing with greater concentrations of substance as set forth in Table I of Example IV.

EXAMPLE VI

Preparation of Colognes and Handkerchief Perfumes

Compositions as set forth in Table I of Example IV are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example IV are imparted to the colognes and to the handkerchief perfumes at all levels indicated.

EXAMPLE VII

Preparation of Soap Compositions

One hundred grams of soap chips (per sample) IVORY ®, produced by the Procter & Gamble Company of Cincinnati, Ohio), are each mixed with one gram samples of substances as set forth in Table I of Example IV until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example IV.

EXAMPLE VIII

Preparation of Solid Detergent Compositions

Detergents are prepared using the following ingredients according to Example I of Canadian Pat. No. 1,007,948 (incorporated by reference herein):

| Ingredient | Percent by Weight |
|---|---|
| "Neodol ® 45-11" (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example IV. Each of the detergent samples has an excellent aroma as indicated in Table I of Example IV.

EXAMPLE IX

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:

1. a water "dissolvable" paper ("Dissolvo paper")
2. Adogen 448 (m.p. about 140° F.) as the substrate coating; and
3. an outer coating having the following formulation (m.p. about 150° F.);
   57% $C_{20-22}$ HAPS
   22% isopropyl alcohol
   20% antistatic agent
   1% of one of the substances as set forth in Table I of Example IV.

Fabric softening compositions prepared according to Example I at column 15 of U.S. Pat. No. 3,632,396 having aroma characteristics as set forth in Table I of Example IV, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example IV is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener nonwoven fabrics and these aroma characteristics are described in Table I of Example IV, supra.

EXAMPLE X

Hair Spray Formulations

The following hair spray formulation is prepared by first dissolving PVP/VA E-735 co-polymer manufactured by the GAF Corporation of 140 West 51st Street, New York, N.Y. in 91.62 grams of 95% food grade ethanol. 8.0 grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America Corporation) | 0.03 weight percent |
| One of the perfumery substances as set forth in Table I of Example IV, supra | 0.10 weight percent |

The perfuming substances as set forth in Table I of Example IV add aroma characteristics as set forth in Table I of Example IV which are rather intense and aesthetically pleasing to the users of the soft-feel, good-hold pump hair sprays.

EXAMPLE XI

Conditioning Shampoos

Monamide CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

Gafquat ®755 N polymer (manufactured by GAF Corporation) of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "Composition B".

The resulting Composition A and Composition B are then mixed in a 50:50 weight ratio of A:B and cooled to 45° C. and 0.3 weight percent of perfuming substance as set forth in Table I of Example IV is added to the mixture. The resulting mixture is cooled to 40° C. and blending is carried out for an additional one hour in each case. At the end of this blending period, the resulting material has a pleasant fragrance as indicated in Table I of Example IV.

EXAMPLE XII

Scented polyethylene pellets having a pronounced scent as set forth in Table I of Example IV are prepared as follows:

75 pounds of polyethylene of a melting point of about 220° F. are heated to about 230° F. in a container of the kind illustrated in FIGS. 11 and 12. 25 pounds of each of the perfume materials of Table I of Example IV supra, are then added quickly to the liquified polyethylene. The lid 228 is put in place and the agitating means 273 are actuated. The temperature is maintained at about 225° F. and the mixing is then continued for about 5-15 minutes. The valve 230 is then opened to allow flow of the molten polyethylene enriched with each of the aroma substance-containing materials to exit through the orifices 234. The liquid falling through the orifices 234 solidify almost instantaneously upon impact with the moving, cooled conveyor 238. Solid polyethylene beads or pellets 244 having pronounced aromas as set forth in Table I of Example IV supra are then formed. Analysis demonstrates that the pellet contain about 25% of each of the perfume substances of Table I of Example IV so that almost no losses of the scenting substance occur. These pellets may be called master pellets.

50 pounds of the scent-containing master pellets are then added to 1,000 pounds of unscented polyethylene powder and the mass is heated to the liquid state. The liquid is molded into thin sheets or films. The sheets or films have a pronounced aroma as set forth in Table I of Example IV supra. The sheets are also fabricated into garbage bags which have aromas as set forth in Table I of Example IV supra.

EXAMPLE XIII

The following basic pear flavor formulation is prepared:

| Ingredients | Parts by Weight |
|---|---|
| Vanillin | 2.0 |
| Hexyl Acetate | 8.0 |
| Hexyl Isobutyrate | 20.0 |
| Trans-2-hexenal (10% in propylene glycol) | 2.0 |
| n-Hexanal | 0.5 |
| Apple Fusel Oil | 10.0 |
| Linalyl Isobutyrate | 0.5 |
| Hexyl-2-methylbutyrate | 10.0 |
| Sauge Sclaree (10% in propylene glycol) | 0.5 |
| Coriander Oil | 0.5 |
| Food grade ethyl alcohol (aqueous, 95%) | 146.0 |
| Propylene glycol | 800.0 |

To a portion of the above basic pear formulation 0.02% by weight of a cis:trans 50:50 mixture of the compound having the structure:

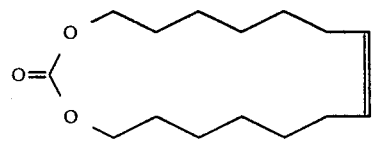

is added. To another portion of the basic pear formulation nothing is added. Both flavor formulations are compared at the rate of 50 ppm in water and evaluated by a blind bench panel of four experienced tasters. All of the tasters of the bench panel state that the flavor containing the mixture of cis and trans isomers of the compound having the structure:

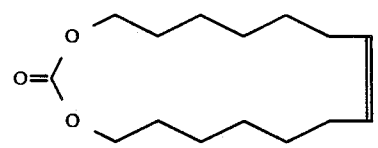

has a more natural, riper pear character. This pear character is enhanced and longer lasting as a result of the additon of the mixture of cis and trans isomers of the compound having the structure:

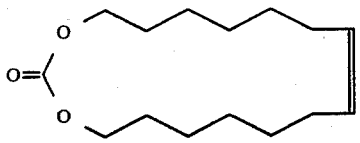

Therefore, the flavor formulation containing the mixture of cis and trans isomers of the compound having the structure:

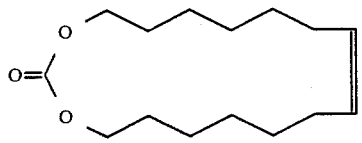

is unanimously preferred.

EXAMPLE XIV

A. Powder Flavor

Twenty grams of the flavor composition of Example XIII which flavor composition contains a mixture of cis and trans isomers of the compound having the structure:

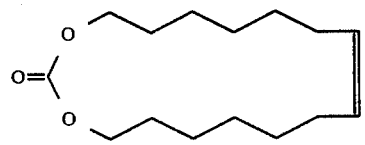

is emulsified in a solution containing 300 grams gum acacia and 700 grams water. The emulsion is spray-dried with a Bowen Lab Model Drier utilzing 250 c.f.m. of air with an inlet temperature of 500° F. and outlet temperature of 200° F. and a wheel speed of 50,000 r.p.m.

B. Paste Blend

The following mixture is then prepared:

| Ingredients | Parts by Weight |
|---|---|
| Liquid flavor composition of Example XIII | 48.4 |
| Cab-O-Sil M-5 (Brand of Silica produced by the Cabot Corporation of 125 High Street, Boston, Mass. 02110); Physical properties: Surface area: 200m²/gm Nominal particle Size: 0.012 microns Density: ⅜ lbs./cu.ft. | 3.2 |

The Cab-O-Sil is dispersed in the liquid flavor composition with vigorous stirring, thereby resulting in a viscous liquid. 48.4 parts by weight of the powder flavor composition prepared in Part A is then blended into the said viscous liquid with stirring at 25° C. for a period of 30 minutes, resulting in a thixotropic sustained released flavor paste.

EXAMPLE XV

Chewing Gum 100 parts by weight of chicle are mixed with 4 parts by weight of the flavor prepared in accordance with Example XIVB. 300 parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long-lasting pear flavor.

EXAMPLE XVI

Toothpaste Formulation

The following separate groups of ingredients are prepared:

| | |
|---|---|
| Group "A" | |
| 30.200 | Glycerin |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium n-Lauroyl Sarcosinate (foaming agent) |
| Group "D" | |
| 1.200 | Flavor Material of Example XIVB |
| 100.00 | (Total) |

Procedure

1. To ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant pear flavor of constant strong intensity throughout said procedure (1–1.5 minutes).

EXAMPLE XVII

Chewable Vitamin Tablets

The flavor material produced according to the process of Example XIVB is added to a chewable vitamin tablet formulation at a rate of 5 gm/kg which chewable vitamin tablet formulation is prepared as follows:

| Ingredients | Gms/1000 Tablets |
|---|---|
| Vitamin C (ascorbic acid) as ascorbic acid-solution mixture 1:1 | 70.0 |
| Vitamin $B_1$ (thiamine mononitrate) | 4.0 |

| Ingredients | Gms/1000 Tablets |
|---|---|
| as Rocoat ® thiamine mononitrate 33⅓% (Hoffman La Roche) | |
| Vitamin B$_2$ (riboflavin) | 5.0 |
| as Rocoat ® riboflavin 33-⅓% | |
| Vitamin B$_6$ (pyridoxine hydrochloride) | 4.0 |
| as Rocoat ® pyridoxide hydrochloride 33-⅓% | |
| Niacinamide | 33.0 |
| as Rocoat ® niacinamide 33-⅓% | |
| Calcium pantothenate | 11.5 |
| Vitamin B$_{12}$ (cyanocobalamin) | 3.5 |
| as Merck 0.1% in gelatin | |
| Vitamin E (dl-alpha tocopheryl acetate | 6.6 |
| as dry Vitamin E acetate 33-⅓% Roche | |
| d-Biotin | 0.044 |
| Certified lake color | 5.0 |
| Flavor of Example XIVB | 5.0 |
| Sweetener-sodium saccharin | 1.0 |
| Magnesium stearate lubricant | 10.0 |

| Ingredients | Gms/1000 Tablets |
|---|---|
| Mannitol q.s. to make | 500.0 |

Preliminary tablets are prepared by slugging, with flatfaced punches and grinding the slugs to 14 mesh. 13.5 grams dry Vitamin A acetate and 0.6 grams Vitamin D are then added as beadlets. The entire blend is then compressed using concave punches at 0.5 grams each.

Chewing of the resultant tablet yields a pleasant, long-lasting, consistently strong pear flavor for a period of 12 minutes.

What is claimed is:

1. The compound having the structure:

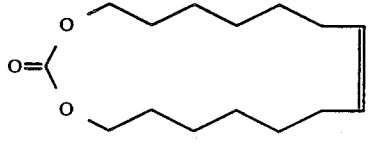

* * * * *